United States Patent [19]

Peart

[11] Patent Number: 5,288,953
[45] Date of Patent: Feb. 22, 1994

[54] COMPRESSIBLE STETHOSCOPE EAR TIP

[75] Inventor: Edward L. Peart, Arden, N.C.

[73] Assignee: Welch Allyn, Inc., Skaneateles Falls, N.Y.

[21] Appl. No.: 875,650

[22] Filed: Apr. 29, 1992

[51] Int. Cl.$^5$ ................ H04R 25/02; A61B 7/02
[52] U.S. Cl. ................ 181/130; 181/131; 181/135
[58] Field of Search ........... 181/130, 131, 135, 137; 128/864, 865, 866, 867

[56] References Cited

U.S. PATENT DOCUMENTS

| | | | |
|---|---|---|---|
| 2,803,308 | 8/1957 | Di Mattia | 181/135 |
| 2,888,921 | 6/1959 | Nielson et al. | 128/865 |
| 3,123,069 | 3/1964 | Laisne et al. | 128/865 |
| 3,303,902 | 2/1967 | Knott | 181/135 |
| 3,710,888 | 1/1973 | Peart | 181/131 |
| 4,852,684 | 0/1989 | Packard | 181/131 |
| 4,913,259 | 0/1990 | Packard | 181/131 |

Primary Examiner—Michael L. Gellner
Assistant Examiner—Eddie C. Lee
Attorney, Agent, or Firm—Harris Beach & Wilcox

[57] ABSTRACT

An ear tip for use on stethoscopes, audio head sets and similar apparatus is shown having a relatively rigid inner body and an outer flexible soft body that can compress to accommodate outer ear canal configurations in comfort and efficient sealing contact without hinging or folding over so as to restrict sound transmission therethrough. A tubular guiding ferrule configuration insures proper alignment and maintenance of sound transmission efficiency with user comfort.

12 Claims, 2 Drawing Sheets

COMPRESSIBLE STETHOSCOPE EAR TIP

BACKGROUND OF THE INVENTION

This invention relates to an ear tip for attachment to a sound transmitting device such as a stethoscope, audio headset, or similar device. Stethoscopes and audio headsets typically comprise a pair of ear tubes spring loaded together with a compressible ear tip mounted on the ends of the ear tubes so as to form a soundproof seal with the user's ear and the sound transmitting tube of the stethoscope or head set. It is generally desired to create a soundproof seal with the user's ear so that the wearer can hear the transmitted sound as free of ambient interference as possible. Two basic problems have been encountered with this type of device; namely, serious discomfort to the user from relative hardness of the ear tip when soundproof sealing is sought and sound transmission and sealing against ambient interference when user comfort is paramount.

A large number of patents directed to these general problems have been developed over the years. One of the more recent ear tips directed to this problem is that shown in U.S. Pat. No. 4,852,684 issued Aug. 1, 1989 to Packard. This patent discloses a sophisticated and complicated ear tip having very specific requirements for wall thickness, hardness and flexibility of the ear contacting bulbous portion in order to provide the desired combination of comfort and acoustic sealing characteristics.

OBJECTS AND SUMMARY OF THE INVENTION

The present invention is directed to an ear tip that permits efficient delivery of sound to a human ear with comfort. The ear tip of the present invention eliminates the need for precisely controlled wall thickness and special elastomeric material specifications.

It is therefore an object of the present invention to provide an improved ear tip that overcomes the disadvantages of the prior art.

It is another object of the present invention to provide a simplified construction which permits use of standard materials with uniform wall thicknesses and which allows unobstructed transmission of sound therethrough.

It is another object of the present invention to provide an ear tip construction such that it does not fold over and obstruct the sound passageway through the tip, even when subjected to substantial side pressures.

It is another object of the present invention to provide an ear tip for stethoscopes, audio head sets and the like in which a bulbous compressible ear contacting surface is provided that can be easily deformed to match the ear canal entrance of a user without restricting the sound transmission characteristics.

In one embodiment, these objects and advantages of the present invention are attained by the provision of a generally rigid inner body made of aluminum, plastic or similar material covered with an outer body of elastomeric material. The elastomeric body is formed with a sleeve section wrapped about the inner body and a convex hollow end section adapted to contact the ear canal entrance of a user in a readily conforming manner. Axial alignment of the sound transmission passageway through the ear tip is maintained by an inner cylindrical sleeve portion of the end section that slidingly cooperates with one end of the inner body member. The inner body member carries at its other end a threaded receptacle for cooperative mounting on a stethoscope ear tube or the like.

BRIEF DESCRIPTION OF THE DRAWINGS

Further objects of the present invention, together with additional advantages thereof will be apparent by reference to the following detailed description of a preferred embodiment and the drawings wherein.

DETAILED DESCRIPTION OF A PREFERRED EMBODIMENT

Figure 1:
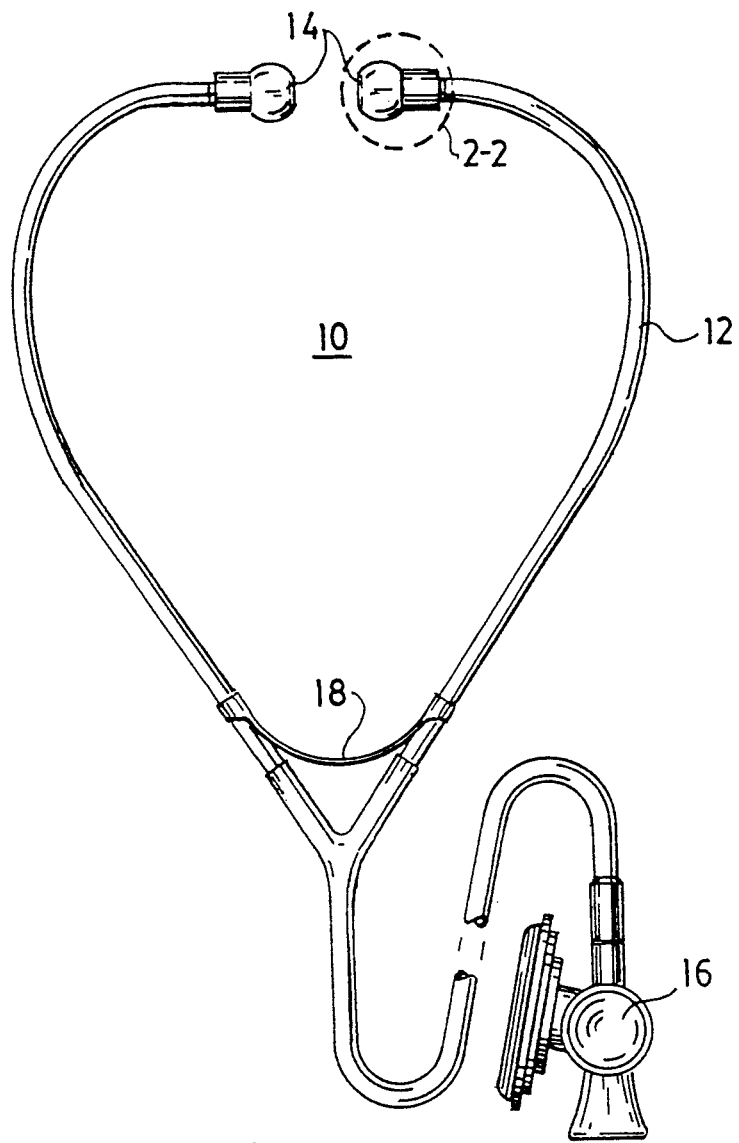
FIG. 1 is a view of a stethoscope with ear tips according to the present invention.

Referring now to FIG. 1, there is shown a stethoscope 10 having a pair of ear tubes 12 with ear tips 14 mounted on the upper ends thereof for insertion in the ears of a user for permitting transmission of sound from the pickup device 16 to the ear of the user. The usual spring mechanism 18 is shown urging the ear tubes 12 together so as to urge the ear tips 14 into the ear canal of the user and to seal out ambient noise.

Figure 2:
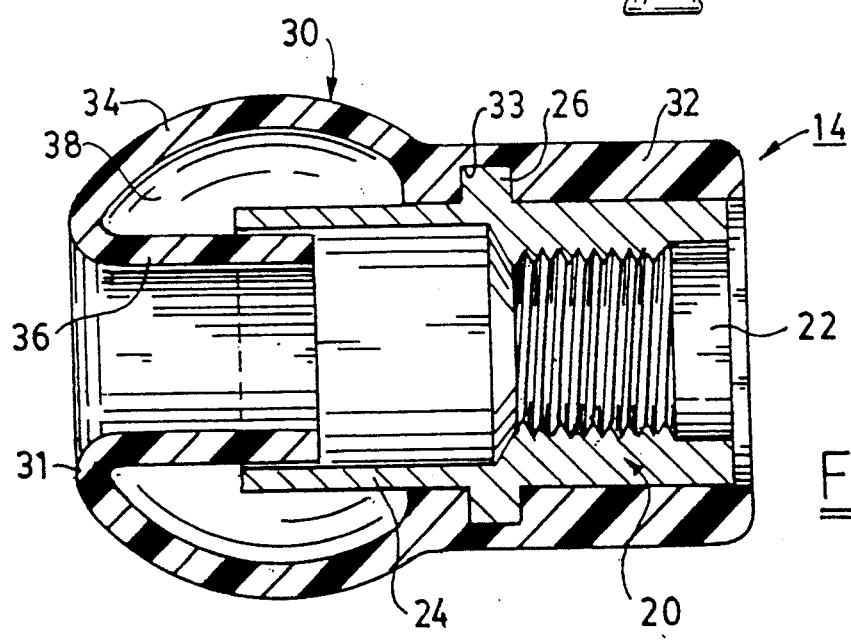
FIG. 2 is a cross section of a first embodiment tip 2—2 of FIG. 1 showing the ear tip in detail.

Referring now to FIG. 2, the ear tip 14 according to the present invention comprises an inner body member 20 and an outer body member 30. Body member 20 is usually made of aluminum or a rigid plastic. Body member 20 has at the right hand end in FIG. 2 a threaded receptacle portion 22 for reception of the threaded end of an ear tube 12. Alternatively, ear tip 14 could be secured on tube 12 by a snap ring, glue or a press fit as is well known in the art. The other end of the body portion 20 has a smooth cylindrical ferrule 24 adapted to extend partway into the resilient ear contacting portion 31 of the body 30. A flange 26 extends radially outwardly from the inner body 20 and as will be described herein, acts as a key for the outer body member 30 to prevent axial movement thereof relative to the inner body member. The inner body 20 is covered by outer body 30 which is generally formed of an elastomeric material that can be readily deformed and which forms a resilient shell and covering about the rigid inner body 20.

Figure 3:
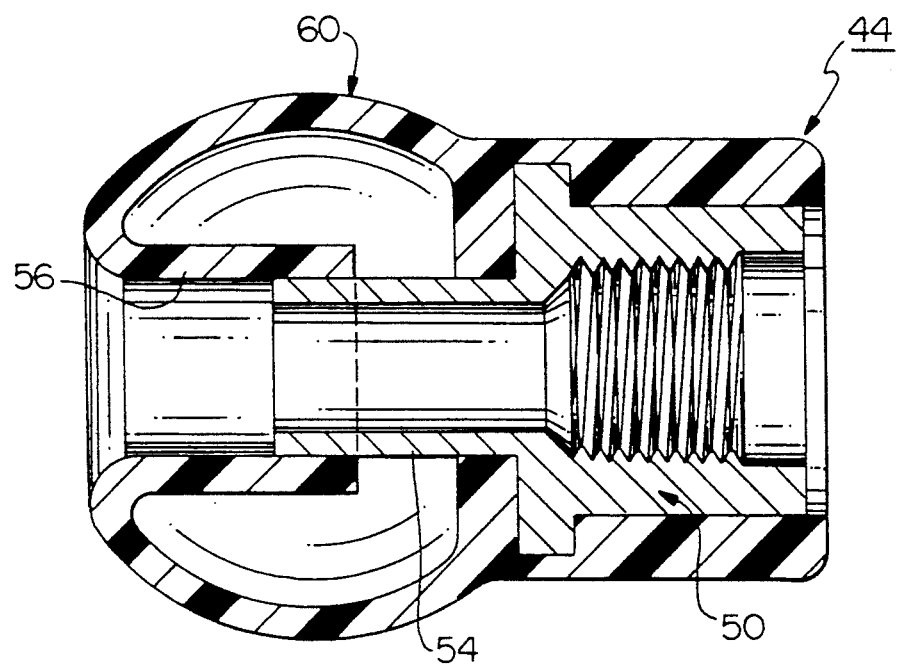
FIG. 3 is a cross section of the tip 2—2 of a second embodiment of the instant invention showing the ear tip in detail.

Outer body 30 has a sleeve portion 32 which mates with and engages about the receptacle end 22 of the inner body 20 and has a mating groove or recess 33 which mates with the flange 26 to maintain axial alignment of the inner and outer bodies. The left hand end of the outer body member 30 comprises a generally convex wall portion 34 extending from adjacent the recess 33 to the ear contacting end 31 of the outer body member 30. The left hand end of the body member 30 in FIG. 2 is turned back in on itself to form a cylindrical ferrule portion 36 which extends back into the interior of the inner body 20. Tubular ferrule 36 in FIG. 2 is sized to fit within the ferrule portion 24 of the inner body 20 and is sized so as to easily move axially within the ferrule portion 24. Alternatively as shown in the second embodiment 44 of FIG. 3, ferrule 56 of the outer body member 60 can be sized to slidably fit about the outside of ferrule 54 of inner body member 50. The outer convex wall 34 is smoothly formed about the end thereof to smoothly transition into the tubular ferrule portion 36 so as to provide a comfortable smooth surface for contact with the exterior surface of the ear canal of a user.

The hollow interior compartment 38, formed by the convex wall 34 and ferrule 36 of the outer member 30, allows the wall 34 to collapse by flexing so as to provide an increased surface area contact or cushion about the entrance to the ear canal of a user. This compressing and folding action is assisted by the ferrule 36 sliding into the ferrule 24. Ferrule 36, as it slides into ferrule 24, prevents the end 31 of body 30 from lateral hinging or folding over so as to restrict the sound passageway therethrough. Sufficient clearance is provided between the respective ends of the ferrules 24 and 36 so that the tip 31 does not bottom out as it is compressed toward the inner body member 20 in normal use. The material used in the outer body 30 can be any one of a number of elastomer materials such as natural rubber, vinyl, polyurethane, silicone or nitrile rubbers or other thermoplastic materials. The thickness of wall 34 and the material from which it is made are chosen to provide comfort to the user by controlled flattening and deforming of the end 31 of the outer body 30 at the left hand end of FIG. 2 as the ear piece is directed into the outer ear canal of a user. It is apparent that with this soft telescoping and deforming action, contact over a large surface of the outer ear canal area is achieved. This offers comfort and efficient acoustic sealing to the ear of the user, while preventing undesired folding and collapsing of the sound passageway. The maximum possible amount of sound energy is thus transmitted through the ear tip to the user.

It will thus be seen that an ear tip has been provided that can be simply and easily molded from simple, yet functional parts in an economical fashion without the necessity of closely controlled tolerances, wall thicknesses or elastomeric material characteristics and yet will allow comfortable efficient transmission of sound therethrough from pickup to the ear of the user.

While this invention has been explained with reference to the structure disclosed herein, it is not confined to the details set forth and this application is intended to cover any modifications and changes as may come within the scope of the following claims:

I claim:

1. An ear tip for use with a headset type device which comprises:
   a generally tubular inner body member having a receptacle portion at a first end for receiving therein the end of an ear tube and an extended open ferrule at a second end, wherein said inner body member receptacle portion is threaded to screw onto a similarly threaded ear tube;
   an outer body member having a sleeve portion and an enlarged ear contacting portion, wherein said sleeve portion is formed to engage about said inner body member receptacle portion;
   said outer body ear contacting portion extending outwardly beyond the open ferrule end of said inner body member;
   said inner body member being formed of a generally rigid material and said outer body being formed of a resilient material; and
   said ear contacting portion of said outer body member comprising:
   a convex outer wall forming a hollow chamber about the open end of said inner body ferrule;
   said convex outer wall being turned inwardly to form a tubular ferrule slidably engaging said open ferrule of said inner body;
   said convex outer wall having a thickness and flexibility so as to permit a cushioning deformation about the ear canal opening of a user when installed on the ear tube of a headset type device positioned in the ear of a user; and
   a tubular inner ferrule portion is formed to slidably engage with the inside of said open ferrule end of said inner body.

2. An ear tip for use with a headset type device which comprises:
   a generally tubular inner body member having a receptacle portion at one end for receiving therein the end of an ear tube and an extended open ferrule at the other end;
   an outer body member having a sleeve portion and an enlarged ear contacting portion;
   said outer body ear contacting portion extending outwardly beyond the open ferrule end of said inner body member;
   said inner body member being formed of a generally rigid material and said outer body being formed of a resilient material; and
   said ear contacting portion of said outer body member having a convex outer surface and a tubular inner ferrule portion;
   wherein said outer body tubular inner ferrule portion is formed by turning back into itself said outer convex surface at the ear contacting end of said outer body member to form said tubular ferrule inside a convex cylindrical chamber and said tubular ferrule is formed to slidably engage with the inside of said open ferrule end of said inner body to provide lateral support of said ear contacting portion while allowing axial movement thereof.

3. An ear tip according to claim 2 wherein said tubular inner ferrule portion of said outer body member is formed to slidably engage with the inside of said open ferrule end of said inner body.

4. An ear tip according to claim 2 wherein said tubular inner ferrule portion of said ear contacting portion of said outer body member extends inwardly relative to the open ferrule end of said inner body member a distance sufficient to prevent folding over of said convex outer wall to close off the audio passageway therethrough.

5. An ear tip according to claim 2 wherein said tubular inner ferrule portion of said outerbody member is formed to slidably engage about the outer surface of said open ferrule end of said inner body.

6. An ear tip according to claim 5 wherein said tubular inner ferrule portion of said ear contacting portion of said outer body member extends inwardly relative to the open ferrule end of said inner body member a distance sufficient to prevent folding over of said convex outer wall to close off the audio passageway therethrough.

7. An ear tip according to claim 2 wherein said inner body member receptacle portion is threaded to screw onto a similarly threaded ear tube.

8. An ear tip to claim 2 wherein said inner body is formed from the group consisting of a metal and a rigid plastic and said outer body is formed of an elastomeric material from the group consisting of rubber, vinyl, polyurethane, silicon rubber, and nitrile rubber.

9. An ear tip according to claim 2 wherein said generally tubular inner body and said tubular inner ferrule of said outer body form an unobstructed sound passageway from an ear tube to a user's ear canal when installed thereon.

10. An ear tip according to claim 2 wherein said inner body member has a radially extending flange approximately at the midpoint thereof; and said outer body member has a mating recess, so that said outer body member is fixed from axial movement relative to said inner body member.

11. An ear tip according to claim 2 wherein said inner body ferrule portion has a diameter sufficiently greater than the inside diameter of an ear tube inserted in said inner body receptacle portion so that the inside diameter of said outer body tubular inner ferrule is equal to or greater than said ear tube diameter.

12. An ear tip according to claim 2 wherein the inside diameter of said tubular inner ferrule portion of said ear contacting portion of said outer body member is less than the inside diameter of an ear tube inserted in said inner body receptacle portion.

* * * * *